United States Patent
Coelho Tsou et al.

(10) Patent No.: US 8,575,411 B2
(45) Date of Patent: *Nov. 5, 2013

(54) METHOD FOR REACTING NATURAL GAS TO AROMATICS WHILE ELECTROCHEMICALLY REMOVING HYDROGEN AND ELECTROCHEMICALLY REACTING THE HYDROGEN WATER

(75) Inventors: Joana Coelho Tsou, Heidelberg (DE); Alexander Panchenko, Ludwigshafen (DE); Annebart Engbert Wentink, Mannheim (DE); Sebastian Ahrens, Wiesloch (DE); Thomas Heidemann, Viernheim (DE)

(73) Assignee: BASF SE, Ludwigshafen (DE)

( * ) Notice: Subject to any disclaimer, the term of this patent is extended or adjusted under 35 U.S.C. 154(b) by 119 days.

This patent is subject to a terminal disclaimer.

(21) Appl. No.: 13/256,536

(22) PCT Filed: Mar. 29, 2010

(86) PCT No.: PCT/EP2010/054092
§ 371 (c)(1),
(2), (4) Date: Sep. 14, 2011

(87) PCT Pub. No.: WO2010/115747
PCT Pub. Date: Oct. 14, 2010

(65) Prior Publication Data
US 2012/0004482 A1    Jan. 5, 2012

(30) Foreign Application Priority Data
Apr. 6, 2009 (EP) .................................. 09157396

(51) Int. Cl.
*C07C 2/76* (2006.01)
(52) U.S. Cl.
USPC ............ 585/407; 585/408; 585/818; 585/943
(58) Field of Classification Search
USPC .................................. 585/407, 408, 818, 943
See application file for complete search history.

(56) References Cited

U.S. PATENT DOCUMENTS

| 4,899,006 | A | 2/1990 | Dave et al. |
| 7,019,184 | B2 | 3/2006 | Allison et al. |
| 2011/0060176 | A1 | 3/2011 | Kiesslich et al. |
| 2011/0124933 | A1 | 5/2011 | Kiesslich et al. |
| 2012/0004482 | A1 | 1/2012 | Tsou et al. |

FOREIGN PATENT DOCUMENTS

WO     03 084905     10/2003

OTHER PUBLICATIONS

Solymosi, F., et al., "Conversion of ethane into benzene on Mo2/ZSM-5 catalyst," Applied Catalysis A: General, vol. 166, No. 1, pp. 225-235, (Jan. 2, 1998) XP023613553.
Wang, D., et al., "Characterization of a Mo/ZSM-5 Catalyst for the Conversion of Methane to Benzene," Journal of Catalysis, vol. 169, pp. 347-358, (1997).
Stookey, D. J., et al., "Membranes: Gas-Separation Applications," Ullmann's Encyclopedia of Industrial Chemistry, Wiley-VCH Verlag GmbH & Co. KGaA, Weinheim, pp. 1-12, (2005).
Ibeh, B., et al., "Separation of hydrogen from a hydrogen/methane mixture using a PEM fuel cell," International Journal of Hydrogen Energy, vol. 32, pp. 908-914, (2007).
International Search Report Issued Sep. 3, 2010 in PCT/EP10/054092 filed Mar. 29, 2010.
U.S. Appl. No. 13/383,014, filed Jan. 9, 2012, Kubanek, et al.
U.S. Appl. No. 13/383,321, filed Jan. 10, 2012, Kubanek, et al.
U.S. Appl. No. 13/260,053, filed Sep. 23, 2011, Coelho Tsou, et al.
U.S. Appl. No. 13/202,427, filed Aug. 19, 2011, Coelho Tsou, et al.
U.S. Appl. No. 13/259,863, filed Sep. 23, 2011, Coelho Tsou, et al.
U.S. Appl. No. 13/186,592, filed Jul. 20, 2011, Schneider, et al.

*Primary Examiner* — Thuan D Dang
(74) *Attorney, Agent, or Firm* — Oblon, Spivak, McClelland, Maier & Neustadt, L.L.P.

(57) ABSTRACT

The invention relates to a process for converting aliphatic hydrocarbons having from 1 to 4 carbon atoms into aromatic hydrocarbons, which comprises the steps:
 a) reaction of a feed stream E comprising at least one aliphatic hydrocarbon having from 1 to 4 carbon atoms in the presence of a catalyst under nonoxidative conditions to give a product stream P comprising aromatic hydrocarbons and hydrogen and
 b) electrochemical removal of at least part of the hydrogen formed in the reaction from the product stream P by means of a gastight membrane-electrode assembly comprising at least one selectively proton-conducting membrane and at least one electrode catalyst on each side of the membrane, where at least part of the hydrogen is oxidized to protons over the anode catalyst on the retentate side of the membrane and the protons are, after passing through the membrane on the permeate side, reacted with oxygen to form water over the cathode catalyst, with the oxygen originating from an oxygen-comprising stream O which is brought into contact with the permeate side of the membrane.

23 Claims, No Drawings

METHOD FOR REACTING NATURAL GAS TO AROMATICS WHILE ELECTROCHEMICALLY REMOVING HYDROGEN AND ELECTROCHEMICALLY REACTING THE HYDROGEN WATER

This application is a 371 of PCT/EP2010/054092 filed Mar. 29, 2010. Priority to European patent application 09157396.4, filed Apr. 6, 2009, is claimed.

The present invention relates to a process for converting aliphatic hydrocarbons having from 1 to 4 carbon atoms into aromatic hydrocarbons in the presence of a catalyst under nonoxidative conditions, wherein at least part of the hydrogen formed in the reaction is separated off electrochemically by means of a membrane-electrode assembly and the hydrogen is reacted with oxygen to form water and generates electric power.

Aromatic hydrocarbons such as benzene, toluene, ethylbenzene, styrene, xylene and naphthalene are important intermediates in the chemical industry and demand for them is continuing to rise. In general, they are obtained by catalytic reforming of naphtha which is in turn obtained from petroleum. Recent studies have shown that worldwide petroleum reserves are more limited than natural gas reserves. The preparation of aromatic hydrocarbons from starting materials which can be obtained from natural gas is therefore an alternative which has now become economically interesting. The main component of natural gas is usually methane.

One possible reaction route for obtaining aromatics from aliphatics is nonoxidative dehydroaromatization (DHAM). The reaction is in this case carried out under nonoxidative conditions, in particular with exclusion of oxygen. In DHAM, dehydrogenation and cyclization of the aliphatics to form the corresponding aromatics takes place with liberation of hydrogen. 1 mol of benzene and 9 mol of hydrogen are formed from 6 mol of methane.

Examination of the thermodynamics shows that the reaction is limited by the position of the equilibrium (D. Wang, J. H. Lunsford and M. P. Rosynek, "Characterization of a Mo/ZSM-5 catalyst for the conversion of methane to benzene", Journal of Catalysis 169, 347-358 (1997)). Calculations for the components methane, benzene, naphthalene and hydrogen show that the equilibrium conversions for the isothermal conversion of methane into benzene (and naphthalene) decrease with increasing pressure and decreasing temperature; for example, the equilibrium conversion at 1 bar and 750° C. is about 17%.

To utilize the methane which is not reacted in the reaction efficiently, i.e. to reuse it for the DHAM, a major part of the $H_2$ comprised in the reaction product mixture should be removed, since otherwise the reaction equilibrium is shifted unfavorably in the direction of methane by the $H_2$ and the yield of aromatic hydrocarbons is therefore lower.

A process for the DHAM of hydrocarbons, in particular natural gas, with separation of the $H_2$ and the aromatic hydrocarbons from the product gas and recirculation of the remaining product gas to the reaction zone or the renewed reaction of the product gas after removal of the hydrogen and without prior removal of the aromatic hydrocarbons in a further reaction stage is described in U.S. Pat. No. 7,019,184 B2. As methods for separating off the $H_2$, mention is made of hydrogen-selective membranes and pressure swing adsorption. The hydrogen which has been separated off can be used for energy generation, for example in a combustion chamber or in a fuel cell.

In the removal of hydrogen by means of a selective hydrogen-permeable membrane, the hydrogen migrates as $H_2$ molecules through the membrane. The diffusion rate depends on the partial pressure difference of hydrogen between retentate side and permeate side of the membrane. This can in principle be influenced by three different methods: 1) compression of the feed gas, as a result of which the partial pressure is increased, 2) generation of a vacuum on the permeate side or 3) use of sweep gas on the permeate side, which reduces the partial pressure of hydrogen. These methods are either mechanically demanding (options 1) and 2)) or require separation of the sweep gas from the hydrogen. In addition, appropriate apparatuses for compression and expansion of the gas mixture have to be present. For kinetic reasons, a certain proportion of the hydrogen always remains in the retentate. For example, the permeate of an $H_2/CH_4$ mixture obtained by means of a hydrogen-permeable polymer membrane usually comprises 1 molecule of $CH_4$ per 10 molecules of $H_2$. In the case of a Pd membrane, which becomes selectively hydrogen-permeable above about 200° C. and reaches its optimal separation performance at 400° C.-500° C., the permeate usually comprises 1 molecule of $CH_4$ per 200 molecules of $H_2$.

In pressure swing adsorption, an adsorbent is supplied cyclically in a first phase with the hydrogen-comprising stream, with all components apart from hydrogen being retained by adsorption. In a second phase, these components are desorbed again by means of reduced pressure. This is a technically very complicated process in which adsorbents have to be used and a hydrogen-comprising waste stream whose hydrogen content can be more than 40% is formed, see Ullmann's Encyclopedia of Industrial Chemistry, "Membranes: Gas Separation-Applications", D. B. Strooky, Elah Strategies, page 6, Chesterfield, Mo., USA, 2005 Wiley-VCH Verlag, Weinheim.

Apart from pressure swing adsorption and the use of selective hydrogen-permeable membranes, the use of a "cold box" is also a customary method of separating hydrogen from gas mixtures.

In the removal of hydrogen by means of a cold box, the gas mixture is cooled to a temperature in the range from about −150° C. to −190° C. under pressures of from 30 to 50 bar. Generation of these low temperatures is costly. If the mixture which has in this way been freed of hydrogen is to be reused in a reaction, it has to be reheated to the appropriate reaction temperature, for example to 600-1000° C. for dehydroaromatization.

The separation of hydrogen from a mixture of hydrogen and methane is described by B. Ibeh et al. (International Journal of Hydrogen Energy 32 (2007), pages 908-914). The starting point of these authors was to examine the suitability of natural gas as carrier gas for the transport of hydrogen through the existing infrastructure for natural gas transport, with the hydrogen having to be separated off again from the natural gas after joint transport of the two. B. Ibeh et al. used a fuel cell having a single proton-exchange membrane and Pt or Pt/Ru anode electrocatalysts for separating the hydrogen from hydrogen/methane mixtures. The fuel cell was supplied with hydrogen/methane mixtures at atmospheric pressure and temperatures in the range from 20 to 70° C.

It is an object of the present invention to provide a process for obtaining aromatic hydrocarbons from aliphatic hydrocarbons having from 1 to 4 carbon atoms, which does not have the disadvantages of the processes known from the prior art. The aliphatic hydrocarbons used and also the by-products obtained in the reaction should be utilized efficiently. The process should have a very favorable energy balance and require a very low outlay in terms of apparatus.

The object is achieved according to the invention by the process for converting aliphatic hydrocarbons having from 1 to 4 carbon atoms into aromatic hydrocarbons, which comprises the steps:

a) reaction of a feed stream E comprising at least one aliphatic hydrocarbon having from 1 to 4 carbon atoms in the presence of a catalyst under nonoxidative conditions to give a product stream P comprising aromatic hydrocarbons and hydrogen and b) electrochemical removal of at least part of the hydrogen formed in the reaction from the product stream P by means of a gastight membrane-electrode assembly comprising at least one selectively proton-conducting membrane and at least one electrode catalyst on each side of the membrane, where at least part of the hydrogen is oxidized to protons over the anode catalyst on the retentate side of the membrane and the protons are, after passing through the membrane on the permeate side, reacted with oxygen to form water over the cathode catalyst, with the oxygen originating from an oxygen-comprising stream O which is brought into contact with the permeate side of the membrane.

The particular advantage of the process of the invention is the electrochemical removal of the hydrogen formed from the product stream P with simultaneous generation of electric power.

The hydrogen is not, as known from the prior art, firstly separated off and subsequently fed as hydrogen to a power-generating process such as an external fuel cell or gas turbine but power generation occurs during the separation. Compared to the processes known from the prior art, depending on the point of view, a separation apparatus or a unit for generating energy from the hydrogen formed and the energy and substance losses associated therewith are saved.

The process of the invention thus provides economical utilization of the starting materials used with simultaneous production of valuable aromatic hydrocarbons and electric energy.

The driving force for the electrochemical removal of hydrogen is the potential difference between the two sides of the membrane. Since the removal is not, as in the case of the hydrogen-selective membranes customarily used, dependent on the partial pressure difference between the two sides of the membrane, the removal of hydrogen can be carried out at very much lower pressures and pressure differences, preferably with an externally generated pressure difference being completely dispensed with and in particular the same pressure prevailing on permeate and retentate sides. This significantly reduces the mechanical stress on the membrane, which, inter alia, increases its long-term stability and increases the choice of possible materials for the membrane. This then offers the opportunity of carrying out the removal of the hydrogen at lower pressures than in the case of conventional membranes and has the advantage that the entire process, i.e. the DHAM and the work-up of the product stream P, can be carried out at similar pressures. Complicated apparatuses for compression and expansion of the gas streams can thus be dispensed with.

The electrochemical removal can be carried out at high temperatures compared to removal of the hydrogen by means of a cold box. The temperatures for the electrochemical removal of the hydrogen are usually room temperature or above. The aromatic hydrocarbons formed in the reaction are usually scrubbed out after cooling of the product stream to temperatures below the boiling point of benzene and separated off by means of a gas-liquid separator. Since the electrochemical removal of hydrogen can also be carried out above the temperatures required here, the product stream P does not have to be cooled to a greater extent than is necessary for separating off the aromatic hydrocarbons. Compared to a cold box, cooling steps and the apparatuses required for this purpose are saved. When the product stream P comprising unreacted $C_1$-$C_4$-aliphatics is recirculated to the reaction zone, the recirculated product stream P has to be heated to a significantly lesser extent after removal of the hydrogen and the aromatic hydrocarbons than in the case of removal of the hydrogen by means of a cold box. This saves energy.

Pd membranes are not very suitable for removal of the hydrogen in the present process since they only become hydrogen-permeable above about 200° C., so that only very low flow rates through the membrane can be achieved at these temperatures. However, at the optimal operating temperature of about 400° C.-500° C., undesirable secondary reactions of the aliphatics comprised in the product stream P to be separated can take place at the Pd membranes and lead to relatively rapid formation of excessive carbon deposits on the Pd membranes and to a correspondingly high regeneration requirement.

Compared to removal by means of conventional hydrogen-selective membranes, the electrochemical removal of the hydrogen is significantly more effective and the membrane area required can therefore be reduced at a given separation throughput or significantly more hydrogen can be separated off at a given membrane area, so that the hydrogen content remaining in the recirculated product stream P is significantly lower. Overall, the process of the invention is therefore associated with a lower outlay in terms of apparatus.

The invention is described in detail below.

The reaction of the feed stream E to give a product stream P takes place in the presence of a catalyst under nonoxidative conditions.

For the purposes of the present invention, nonoxidative in relation to the DHAM means that the concentration of oxidants such as oxygen or nitrogen oxides in the feed stream E is below 5% by weight, preferably below 1% by weight, particularly preferably below 0.1% by weight. The feed stream E is very particularly preferably free of oxygen. Particular preference is likewise given to a concentration of oxidants in the feed stream E which is equal to or less than the concentration of oxidants in the source from which the $C_1$-$C_4$-aliphatics originate.

According to the invention, the feed stream E comprises at least one aliphatic having from 1 to 4 carbon atoms. Such aliphatics include, for example, methane, ethane, propane, n-butane, i-butane, ethene, propene, 1- and 2-butene, isobutene. In one embodiment of the invention, the feed stream E comprises at least 50 mol %, preferably at least 60 mol %, particularly preferably at least 70 mol %, very particularly preferably at least 80 mol %, in particular at least 90 mol %, of $C_1$-$C_4$-aliphatics.

Among the aliphatics, particular preference is given to using saturated alkanes. Feed stream E then preferably comprises at least 50 mol %, preferably at least 60 mol %, particularly preferably at least 70 mol %, very particularly preferably at least 80 mol %, in particular at least 90 mol % of alkanes having from 1 to 4 carbon atoms.

Among the alkanes, preference is given to methane and ethane, in particular methane. In this embodiment of the present invention, the feed stream E preferably comprises at least 50 mol %, preferably at least 60 mol %, particularly preferably at least 70 mol %, very particularly preferably at least 80 mol %, in particular at least 90 mol %, of methane.

Natural gas is preferably used as source of the $C_1$-$C_4$-aliphatics. The typical composition of natural gas is as follows: from 75 to 99 mol % of methane, from 0.01 to 15 mol % of ethane, from 0.01 to 10 mol % of propane, up to 6 mol % of butane, up to 30 mol % of carbon dioxide, up to 30 mol % of hydrogen sulfide, up to 15 mol % of nitrogen and up to 5 mol % of helium. Before use in the process of the invention, the natural gas can be purified and enriched by methods known to those skilled in the art. Purification steps include, for example, the removal of any hydrogen sulfide or carbon dioxide and further compounds which are undesirable in the subsequent process which may be present in the natural gas.

The $C_1$-$C_4$-aliphatics comprised in the feed stream E can also originate from other sources, for example can have been obtained in the refining of petroleum. The $C_1$-$C_4$-aliphatics can also have been produced regeneratively (e.g. biogas) or synthetically (e.g. Fischer-Tropsch synthesis).

If biogas is used as $C_1$-$C_4$-aliphatics source, the feed stream E can additionally comprise ammonia, traces of lower alcohols and further components typical of biogas.

In a further embodiment of the process of the invention, LPG (liquefied petroleum gas) can be used as feed stream E. In another embodiment of the process of the invention, LNG (liquefied natural gas) can be used as feed stream E.

Hydrogen, steam, carbon monoxide, carbon dioxide, nitrogen and one or more noble gases can be additionally mixed into the feed stream E.

In step a) of the process of the invention, the feed stream E is reacted under nonoxidative conditions in the presence of a catalyst to give a product stream P comprising aromatic hydrocarbons. This reaction is a dehydroaromatization, i.e. the $C_1$-$C_4$-aliphatics comprised in the feed stream E react with dehydration and cyclization to form the corresponding aromatics, with hydrogen being liberated. According to the invention, the DHAM is carried out in the presence of suitable catalysts. In general, it is possible to use all catalysts which catalyze the DHAM in step a) of the process of the invention. The DHAM catalysts usually comprise a porous support and at least one metal applied thereto. The support usually comprises a crystalline or amorphous inorganic compound.

According to the invention, the catalyst preferably comprises at least one metallosilicate as support. Preference is given to using aluminum silicates as supports. Very particular preference is given according to the invention to using zeolites as supports. Zeolites are aluminum silicates which are usually obtained in the sodium form in their preparation. In the Na form, the excess negative charge present because of the replacement of 4-valent Si atoms by 3-valent Al atoms in the crystal lattice is compensated by Na ions. Instead of sodium alone, the zeolite can also comprise further alkali metal and/or alkaline earth metal ions to balance the charge. According to the invention, the at least one zeolite comprised in the catalysts preferably has a structure selected from among the structure types pentasil and MWW and is particularly preferably selected from among the structure types MFI, MEL, mixed structures of MFI and MEL and MWW. Very particular preference is given to using a zeolite of the ZSM-5 or MCM-22 type. The designations of the structure types of zeolites correspond to those given in W. M. Meier, D. H. Olson and Ch. Baerlocher, "Atlas of Zeolithe Structure Types", Elsevier, 3rd edition, Amsterdam 2001. The synthesis of zeolites is known to those skilled in the art and can be carried out, for example, starting from alkali metal aluminate, alkali metal silicate and amorphous $SiO_2$ under hydrothermal conditions. Here, the type of channel system formed in the zeolite can be controlled via organic template molecules, via the temperature and further experimental parameters.

The zeolites can comprise further elements such as Ga, B, Fe or In in addition to Al.

The zeolites which are preferably used as supports are preferably used in the H form or the ammonium form, in which the zeolites are also commercially available.

In the conversion of the Na form into the H form, the alkali metal and/or alkaline earth metal ions comprised in the zeolite are replaced by protons. A customary process which is preferred according to the present invention for conversion of the catalysts into the H form is a two-stage process in which the alkali metal and/or alkaline earth metal ions are firstly replaced by ammonium ions. On heating the zeolite to about 400-500° C., the ammonium ion decomposes into volatile ammonia and the proton which remains in the zeolite.

For this purpose, the zeolite is treated with an $NH_4$-comprising mixture. As $NH_4$-comprising component of the $NH_4$-comprising mixture, use is made of an ammonium salt selected from the group consisting of ammonium chloride, ammonium carbonate, ammonium hydrogencarbonate, ammonium nitrate, ammonium phosphate, ammonium acetate, ammonium hydrogenphosphate, ammonium dihydrogenphosphate, ammonium sulfate and ammonium hydrogensulfate. Preference is given to using ammonium nitrate as $NH_4$-comprising component.

The treatment of the zeolite with the $NH_4$-comprising mixture is carried out by the known methods suitable for ammonium exchange of zeolites. These include, for example, impregnation, dipping or spreading of the zeolite with an ammonium salt solution, with the solution generally being employed in excess. As solvents, preference is given to using water and/or alcohols. The mixture usually comprises from 1 to 20% by weight of the $NH_4$ component used. The treatment with the $NH_4$-comprising mixture is usually carried out over a period of several hours and at elevated temperatures. After the $NH_4$-comprising mixture has acted on the zeolite, excess mixture can be removed and the zeolite can be washed. The zeolite is subsequently dried at from 40 to 150° C. for a number of hours, usually from 4 to 20 hours. This is followed by calcination of the zeolite at temperatures of from 300 to 700° C., preferably from 350 to 650° C. and particularly preferably from 500 to 600° C. The calcination time is usually from 2 to 24 hours, preferably from 3 to 10 hours, particularly preferably from 4 to 6 hours.

In a particularly preferred embodiment of the present invention, zeolites which have been treated again with an $NH_4$-comprising mixture and subsequently dried are used as supports. The renewed treatment of the zeolites with the $NH_4$-comprising mixture is carried out according to the above description.

Commercially available zeolites in the H form usually have already undergone a first ammonium exchange by treatment with an $NH_4$-comprising mixture with subsequent drying and calcination. Commercially procured zeolites which are present in the H form can therefore be used according to the invention as support a), but they are preferably subjected to renewed treatment with an $NH_4$-comprising mixture and, if appropriate, calcined.

The DHAM catalyst usually comprises at least one metal. The metal is usually selected from groups 3 to 12 of the Periodic Table of the Elements (IUPAC). According to the invention, the DHAM catalyst preferably comprises at least one metal selected from among the transition metals of transition groups 5 to 11. The DHAM catalyst particularly preferably comprises at least one metal selected from the group consisting of Mo, W, Mn, Tc, Re, Fe, Ru, Os, Co, Rh, Ir, Ni, Pd, Pt, Cu, Cr, Nb, Ta, Ag and Au. In particular, the DHAM catalyst comprises at least one metal selected from the group consisting of Mo, W, Re, Fe, Ru, Os, Co, Rh, Ir, Ni, Pd, Pt, Cu.

The DHAM catalyst very particularly preferably comprises at least one metal selected from the group consisting of Mo, W and Re.

It is likewise preferred according to the invention for the DHAM catalyst to comprise at least one metal as active component and at least one further metal as dopant. The active component is, according to the invention, selected from among Mo, W, Re, Ru, Os, Rh, Ir, Pd, Pt. The dopant is, according to the invention, selected from the group consisting of Cr, Mn, Fe, Co, Nb, Ta, Ni, Cu, V, Zn, Zr and Ga, preferably from the group consisting of Fe, Co, Nb, Ta, Ni, Cu and Cr. According to the invention, the DHAM catalyst can comprise more than one metal as active component and more than one metal as dopant. These are each selected from among the metals indicated for the active component and the dopant. The catalyst preferably comprises one metal as active component and one or two metals as dopant.

The at least one metal is, according to the invention, applied wet-chemically or dry-chemically to the support by methods known to those skilled in the art.

In wet chemical methods, the metals are applied in the form of aqueous, organic or organic-aqueous solutions of their salts or complexes by impregnating the support with the corresponding solution. Supercritical $CO_2$ can also serve as solvent. The impregnation can be carried out by the incipient wetness method in which the porous volume of the support is filled with an approximately equal volume of impregnation solution and, if appropriate after aging, the support is dried. It is also possible to employ an excess of solution, in which case the volume of this solution is greater than the porous volume of the support. Here, the support is mixed with the impregnation solution and stirred for a sufficient time. It is also possible to spray the support with a solution of the appropriate metal compound. Other production methods known to those skilled in the art, e.g. precipitation of the metal compounds on the support, spraying-on of a solution comprising metal compound, sol impregnation, etc., are also possible. After application of the at least one metal to the support, the catalyst is dried under reduced pressure or in air at about 80-130° C., usually for from 4 to 20 hours, According to the invention, the at least one metal can also be applied by a dry-chemical method, for example by depositing gaseous metal carbonyls such as $Mo(CO)_6$, $W(CO)_6$ and $Re_2(CO)_{10}$ from the gas phase onto the support at relatively high temperatures. The deposition of the metal carbonyl compound is carried out after calcination of the support. It can also be mixed in the form of a fine powder, for example as carbide, with the support.

According to the invention, the catalyst comprises from 0.1 to 20% by weight, preferably from 0.2 to 15% by weight, particularly preferably from 0.5 to 10% by weight, in each case based on the total weight of the catalyst, of the at least one metal. The catalyst can comprise only one metal; it can also comprise a mixture of two, three or more metals. The metals can be applied together in one solution by wet-chemical means or in different solutions in succession with drying steps between the individual applications. The metals can also be applied in mixed form, i.e. one part can be applied wet-chemically and another part dry-chemically. If necessary, the support can be calcined as described above between the applications of the metal compounds.

According to the invention, the catalyst can comprise at least one metal from the group of active components in combination with at least one metal selected from the group of dopants. In this case, the concentration of the active component is from 0.1 to 20% by weight, preferably from 0.2 to 15% by weight, particularly preferably from 0.5 to 10% by weight, in each case based on the total weight of the catalyst. The dopant is in this case present in the catalyst in a concentration of, according to the invention, at least 0.1% by weight, preferably at least 0.2% by weight, very particularly preferably at least 0.5% by weight, based on the total weight of the catalyst.

In a further preferred embodiment of the present invention, the catalyst is mixed with a binder. Suitable binders are the customary binders known to those skilled in the art, e.g. binders comprising aluminum oxide and/or Si. Particular preference is given to Si-comprising binders, with tetraalkoxysilanes, polysiloxanes and colloidal $SiO_2$ sols being particularly useful.

According to the invention, addition of the binder is followed by a shaping step in which the catalyst composition can be processed by methods known to those skilled in the art to produce shaped bodies. As shaping processes, mention may be made by way of example of spraying of a suspension comprising the support a) or the catalyst composition, spray drying, tableting, pressing in the moist or dry state and extrusion. Two or more of these processes can also be combined. Auxiliaries such as pore formers and pasting agents or other additives known to those skilled in the art can be used for shaping. Possible pasting agents are compounds which lead to an improvement in the mixing, kneading and flow properties. These are preferably, for the purposes of the present invention, organic, in particular hydrophilic polymers such as cellulose, cellulose derivatives such as methylcellulose, starch such as potato starch, wallpaper paste, acrylates, polyacrylates, polymethacrylates, polyvinyl alcohols, polyvinylpyrrolidone, polyisobutylene, polytetrahydrofuran, polyglycol ethers, fatty acid compounds, wax emulsions, water or mixtures of two or more of these compounds. As pore formers, mention may be made for the purposes of the invention of, for example, compounds which can be dispersed, suspended or emulsified in water or aqueous solvent mixtures, e.g. polyalkylene oxides, polystyrene, polyacrylates, polymethacrylates, polyolefins, polyamides, polyesters, carbohydrates, cellulose, cellulose derivatives such as methylcellulose, natural sugar fibers, pulp, graphite or mixtures of two or more of these compounds. Pore formers and/or pasting agents are preferably removed from the shaped body obtained after shaping by means of at least one suitable drying and/or calcination step. The conditions required for this purpose can be selected in a manner analogous to the parameters described above for calcination and are known to those skilled in the art.

Particularly for use as fluidized-bed catalysts, the shaped catalyst bodies are produced by means of spray drying.

The geometry of the catalysts which can be obtained according to the invention can be, for example, spherical (hollow or solid), cylindrical (hollow or solid), ring-, saddle-, star-, honeycomb- or tablet-shaped. Furthermore, extrudates having the shape of, for example, rods, trilobes, quatrolobes, stars or hollow cylinders are possible. The catalyst composition to be shaped can also be extruded, calcined and the extrudates obtained in this way can be crushed and processed to give crushed material or powder. The crushed material can be separated into various sieve fractions.

In a preferred embodiment of the invention, the catalyst is used as shaped bodies or crushed material.

In a further preferred embodiment, the catalyst is used as powder. The catalyst powder can comprise binders, but can also be free of binders.

If the catalyst according to the invention comprises a binder, the latter is present in a concentration of from 5 to 80% by weight, based on the total weight of the catalyst, preferably from 10 to 50% by weight, particularly preferably from 10 to 30% by weight.

It can be advantageous to activate the catalyst used for the dehydroaromatization of $C_1$-$C_4$-aliphatics before the actual reaction.

This activation can be carried out using a $C_1$-$C_4$-alkane such as ethane, propane, butane or a mixture thereof, preferably butane. The activation is carried out at a temperature of from 250 to 850° C., preferably from 350 to 650° C., and a pressure of from 0.5 to 5 bar, preferably from 0.5 to 2 bar. The GHSV (gas hourly space velocity) in the activation is usually from 100 to 4000 $h^{-1}$, preferably from 500 to 2000 $h^{-1}$.

However, it is also possible to carry out an activation by the feed stream E per se already comprising the $C_1$-$C_4$-alkane or a mixture thereof or by adding the $C_1$-$C_4$-alkane or a mixture thereof to the feed stream E. The activation is carried out at a temperature of from 250 to 650° C., preferably from 350 to 550° C., and a pressure of from 0.5 to 5 bar, preferably from 0.5 to 2 bar.

In a further embodiment, it is also possible to add hydrogen in addition to the $C_1$-$C_4$-alkane.

In a preferred embodiment of the present invention, the catalyst is activated by means of a gas stream which comprises $H_2$ and can additionally comprise inert gases such as $N_2$, He, Ne and Ar.

According to the invention, the dehydroaromatization of $C_1$-$C_4$-aliphatics is carried out in the presence of a catalyst at temperatures of from 400 to 1000° C., preferably from 500 to 900° C., particularly preferably from 600 to 800° C., in particular from 700 to 800° C., at a pressure of from 0.5 to 100 bar, preferably from 1 to 30 bar, particularly preferably from 1 to 10 bar, in particular from 1 to 5 bar. According to the present invention, the reaction is carried out at a GHSV (gas hourly space velocity) of from 100 to 10 000 $h^{-1}$, preferably from 200 to 3000 $h^{-1}$.

The dehydroaromatization of $C_1$-$C_4$-aliphatics in step a) can in principle be carried out in all types of reactor known from the prior art. A suitable reactor form is the fixed-bed, radial-flow, tube or shell-and-tube reactor. In these, the catalyst is present as a fixed bed in a reaction tube or in a bundle of reaction tubes. The catalysts can likewise be used as fluidized bed, moving bed or flowing bed in the corresponding reactor types suitable for the particular bed and the process of the invention can be carried out using catalysts present in this form.

According to the invention, the catalyst can be used undiluted or mixed with inert material. The inert material can be any material which is inert, i.e. does not react, under the reaction conditions prevailing in the reaction zones. A suitable inert material is in particular the undoped support used for the catalyst but can also be an inert zeolite, aluminum oxide, silicon dioxide, etc. The particle size of the inert material is in the region of the size of the catalyst particles.

According to the present invention, the undiluted catalyst or catalyst mixed with inert material is preferably present as a fixed, moving or fluidized bed. The catalyst or the mixture of catalyst and inert material is particularly preferably present as a fluidized bed.

The catalyst used in the DHAM is, in one embodiment of the invention, regenerated regularly. The regeneration can be carried out by the customary processes known to those skilled in the art. According to the invention, the regeneration is preferably carried out under reducing conditions by means of a gas stream comprising hydrogen.

The regeneration is carried out at temperatures of from 600° C. to 1000° C. and particularly preferably from 700° C. to 900° C. and pressures of from 1 bar to 30 bar, preferably from 1 bar to 15 bar and particularly preferably from 1 to 10 bar.

The $C_1$-$C_4$-aliphatics are, according to the invention, converted into aromatics with liberation of $H_2$. The product stream P therefore comprises at least one aromatic hydrocarbon selected from the group consisting of benzene, toluene, ethylbenzene, styrene, xylene and naphthalene. It particularly preferably comprises benzene and toluene. The product stream further comprises unreacted $C_1$-$C_4$-aliphatics, hydrogen which has been formed and the inert gases such as $N_2$, He, Ne, Ar comprised in the feed stream E, substances such as $H_2$ which have been added to the feed stream E and impurities originally present in the feed stream E.

In step b) of the process of the invention, at least part of the hydrogen comprised in the product stream P is separated off electrochemically by means of a gastight membrane-electrode assembly (MEA), with the hydrogen to be separated off being transported in the form of protons through the membrane. The product stream P is conveyed along one side of the membrane. This side will hereinafter be referred to as the retentate side. An oxygen-comprising stream O is conveyed along the other side of the membrane, hereinafter referred to as the permeate side. According to the invention, the MEA has at least one selectively proton-conducting membrane. The membrane has at least one electrode catalyst on each side; in the present description, the electrode catalyst located on the retentate side will be referred to as anode catalyst and the electrode catalyst located on the permeate side will be referred to as cathode catalyst. On the retentate side, the hydrogen is oxidized to protons over the anode catalyst, these protons pass through the membrane and on the permeate side react with the oxygen over the cathode catalyst to form water. The driving force is the reduction of oxygen. In the overall reaction, energy is liberated in the form of heat and, by connection of a load, in the form of electric power.

To ensure good contact of the membrane with the hydrogen present on the retentate side and the oxygen on the permeate side, the electrode layers are usually provided with gas diffusion layers. These are, for example, plates having a grid-like surface structure of a system of fine channels or layers of porous material such as nonwoven, woven fabric or paper. The totality of gas diffusion layer and electrode layer is generally referred to as gas diffusion electrode (GDE). The gas diffusion layer conveys the hydrogen to be separated off on the retentate side and the oxygen on the permeate side to close to the membrane and the respective electrode catalyst and aids the outward transport of the hydrogen formed.

Depending on the embodiment of the invention, the anode can also simultaneously serve as an anode catalyst and the cathode can also simultaneously serve as cathode catalyst. However, it is also possible to use different materials for the anode and the anode catalyst and for the cathode and the cathode catalyst.

To produce the electrodes, it is possible to use the customary materials known to those skilled in the art, for example Pt, Pd, Cu, Ni, Fe, Ru, Co, Cr, Fe, Mn, V, W, tungsten carbide, Mo, molybdenum carbide, Zr, Rh, Ag, Ir, Au, Re, Y, Nb, electrically conductive forms of carbon such as carbon black, graphite and nanotubes and also alloys and mixtures of the abovementioned elements.

The anode and cathode can be made of the same material or different materials. The anode catalyst and the cathode catalyst can be selected from among the same or different materials. Particular preference is given to the anode/cathode combinations Pt/Pt, Pd/Pd, Pt/Pd, Pd/Pt , Ni/Ni, Fe/Fe and Ni/Pt.

As electrode catalyst material, it is possible to use the customary compounds and elements known to those skilled in the art which can catalyze the dissociation of molecular hydrogen into atomic hydrogen and the oxidation of hydrogen to protons and also the reduction of oxygen. Suitable materials are, for example, Pd, Pt, Cu, Ni, Fe, Ru, Co, Cr, Mn, V, W, tungsten carbide, Mo, molybdenum carbide, Zr, Rh, Ag, Ir, Au, Re, Y, Nb and also alloys and mixtures thereof, with preference being given according to the invention to Pd and Pt. The elements and compounds mentioned above as electrode catalyst material can also be present in supported form, preferably using carbon as support.

In a preferred embodiment of the present invention, carbon is particularly preferably used as electrodes comprising conductive material. Here, the carbon and an electrode catalyst are preferably applied to a porous support such as nonwoven, woven fabrics or paper. The carbon can be applied as a mixture with the catalyst or the carbon can be applied first and the catalyst can subsequently be applied.

In a further embodiment of the invention, the electrically conductive material used as electrode and the electrode catalyst are applied directly to the membrane.

The membrane is preferably configured as a plate or a tube, with the customary membrane arrangements known from the prior art for the fractionation of gas mixtures, for example tube bundle membranes or plug-in card membranes, being able to be used.

The MEA used according to the invention is gastight, i.e. it has virtually no porosity through which gases in atomic or molecular form can get from one side to the other side of the MEA nor does it have mechanisms by means of which gases can be transported unselectively through the MEA, for example by adsorption, dissolution in the membrane, diffusion and desorption.

The impermeability of the membrane-electrode assembly (MEA) can be ensured by a gastight membrane, by a gastight electrode and/or a gastight electrode catalyst. Thus, for example, a thin metal foil, for example a Pd, Pd—Ag or Pd—Cu foil, can be used as gastight electrode.

The membrane used according to the invention selectively conducts protons, which means, in particular, that it is not an electron conductor. According to the invention, all materials known to those skilled in the art from which proton-conducting membranes can be formed can be used for the membrane. These include, for example, the materials described by J. W. Phair and S. P. S. Badwal in Ionics (2006) 12, pages 103-115. Selectively proton-conducting membranes as are known from fuel cell technology can also be used according to the invention.

It is possible to use, for example, particular heteropolyacids such as $H_3Sb_3B_2O_{14}.10H_2O$, $H_2Ti_4O_9.12H_2O$ and $HSbP_2O_8.10H_2O$; acidic zirconium silicates, phosphates and phosphonates having a layer structure, e.g. $K_2ZrSi_3O_9$, $K_2ZrSi_3O_9$, alpha-$Zr(HPO_4)_2.nH_2O$, gamma-$Zr(PO_4)$—$(H_2PO_4).2H_2O$, alpha- and gamma-Zr-sulfophenylphosphonate or sulfoarylphosphonate, oxide hydrates which do not have a layer structure, e.g. antimonic acid ($Sb_2O_5.2H_2O$), $V_2O_5.nH_2O$, $ZrO_2.nH_2O$, $SnO_2.nH_2O$ and $Ce(HPO_4)_2.nH_2O$. Furthermore, oxo acids and salts which comprise, for example, sulfate, selenate, phosphate, arsenate, nitrate groups, etc., can be used. Oxo anion systems based on phosphates or complex heteropolyacids such as polyphosphate glasses, aluminum polyphosphate, ammonium polyphosphate and polyphosphate compositions such as $NH_4PO_3/(NH_4)_2SiP_4O_{13}$ and $NH_4PO_3/TiP_2O_7$ are particularly useful.

It is also possible to use oxidic materials, such as brownmillerite, fluorite and phosphates having an apatite structure, pyrochlore minerals and perovskites.

Perovskites have the basic formula $AB_{1-x}M_xO_{3-y}$, where M is a trivalent rare earth metal which serves as dopant and y is the oxygen deficiency in the perovskite oxide lattice. A can, for example, be selected from among Mg, Ca, Sr and Ba. B can be selected, inter alia, from among Ce, Zr and Ti. Various elements from the respective groups can also be selected independently for A, B and M.

It is also possible to use structurally modified glasses such as chalcogenide glasses, PbO—$SiO_2$, BaO—$SiO_2$ and CaO—$SiO_2$.

A further class of materials which are suitable for producing gastight and selectively proton-conducting membranes are polymer membranes. Suitable polymers are sulfonated polyether ether ketones (S-PEEK), sulfonated polybenzimidazoles (S-PBI) and sulfonated fluorinated hydrocarbon polymers (NAFION®). Furthermore, it is possible to use perfluorinated polysulfonic acids, polymers based on styrene, poly(arylene ethers), polyimides and polyphosphazenes.

According to the invention, the abovementioned polymers and the phosphate-based compounds are preferably used as materials for the selectively proton-conducting membrane. Very particular preference is given to using membranes comprising polybenzimidazoles, in particular MEAs based on polybenzimidazoles and phosphoric acid, as are marketed, for example, under the name Celtec-P® by BASF SE.

When polymer membranes are used, they are usually moistened by the presence of about 0.5 to 50% by volume of water on the retentate side. The concentration can be set by addition of water to the feed stream E, to the product stream P, to the reaction zone or by recirculation of the product stream P which has been freed of $H_2$ and aromatics and already comprises a certain amount of water from its previous passage through the process. Water is formed on the permeate side, and it is therefore usual for no water to be introduced on this side.

Preference is likewise given to using ceramic membranes. Suitable proton-conducting ceramics are described, for example, in Solid State Ionics 125, (1999), 271-278; Journal of Power Sources 180, (2008), 15-22; Ionics 12, (2006), 103-115; Journal of Power Sources 179 (2008) 92-95; Journal of Power Sources 176 (2008) 122-127 and Electrochemistry Communications 10 (2008) 1005-1007.

Examples of proton-conducting ceramics and oxides are $SrCeO_3$, $BaCeO_3$, $Yb:SrCeO_3$, $Nd:BaCeO_3$, $Gd:BaCeO_3$, $Sm:BaCeO_3$, $BaCaNdO_9$, $Y:BaCeO_3$, $Y:BaZrCeO_3$, Pr-doped Y: $BaCeO_3$, $Gd:BaCeO_3$, $BaCe_{0.9}Y_{0.1}O_{2.95}$ (BYC), $BrCe_{0.95}Yb_{0.05}O_{3-\alpha}$, $BaCe_{0.9}Nd_{0.10}O_{3-\alpha}$, $CaZr_{0.96}In_{0.04}O_{3-\alpha}$, ($\alpha$ denotes the number of oxygen vacancies per formula unit of the oxide of the perovskite type); Sr-doped $La_3P_3O_9$, Sr-doped $LaPO_4$, $BaCe_{0.9}Y_{0.1}O_{3-\alpha}$, (BCY), $BaZr_{0.9}Y_{0.1}O_{3-\alpha}$ (BZY), $Ba_3Ca_{1.18}Nb_{1.82}O_{8.73}$ (BCN18), $(La_{1.95}Ca_{0.05})Zr_2O_{7-\alpha}$, $La_2Ce_2O_7$, $Eu_2Zr_2O_7$, $H_2S/(B_2S_3$ or $Ga_2S_3)/GeS_2$, $SiS_2$, $As_2S_3$ or $CsI$; $BaCe_{0.8}Gd_{0.2}O_{3-\alpha}$(BCGO); Gd-doped $BaCeO_3$ such as $BaCe_{0.85}Y_{0.15}O_{3-\alpha}$(BCY15) and $BaCe_{0.8}Sm_{0.2}O_{3-\alpha}$, $xAl_2O_3$ (1-x)$SiO_2$ (x=0.0-1.0), $SnP_2O_7$, $Sn_{1-x}In_xP_2O_7$ (x=0.0-0.2).

The removal of the hydrogen in step b) of the process of the invention can be carried out at temperatures of from 20 to 1200° C., preferably from 20 to 800° C., particularly preferably from 20 to 500° C. and very particularly preferably at from 70 to 250° C. When MEAs based on polybenzimidazole and phosphoric acid are used, the separation is preferably carried out at from 130 to 200° C.

The removal of the hydrogen in step b) of the process of the invention is preferably carried out at pressures of from 0.5 to 10 bar, more preferably from 1 to 6 bar, particularly preferably from 1 to 4 bar. In a preferred embodiment of the invention, the pressure difference between the retentate side and the permeate side of the membrane is less than 1 bar, preferably less than 0.5 bar, particularly preferably there is no pressure difference.

The oxygen-comprising stream used in step b) comprises, according to the invention, at least 15 mol %, preferably at least 20 mol %, of oxygen. In a preferred embodiment, air or oxygen-enriched air is used as oxygen-comprising stream O. The air is usually used in unpurified form.

The electrochemical removal of the hydrogen in step b) takes place, according to the invention, outside the reaction zone in which step a) is carried out.

According to the invention, at least part of the hydrogen formed in the DHAM is separated off in step b). Preference is given to at least 30%, particularly preferably at least 50%, particularly preferably at least 70% and very particularly preferably at least 95%, in particular at least 98%, being separated off.

The removal of the aromatic hydrocarbons comprised in the product stream P is carried out by the methods known to those skilled in the art.

In one embodiment, the aromatic hydrocarbons formed are separated off from the product stream P between step a) and b). In a further embodiment of the invention, the aromatic hydrocarbons formed are separated off from the product stream P after step b).

In a particularly preferred embodiment of the invention, the product stream P is recirculated to the process after removal of the aromatic hydrocarbons and at least part of the hydrogen; the product stream P is recirculated either to the feed stream E or directly into the reaction zone for the DHAM. It is preferred according to the invention that as much hydrogen as possible be separated off prior to recirculation since hydrogen shifts the reaction equilibrium in the DHAM to the side of the starting materials. The recirculated product stream P preferably comprises from 0 to 2 mol %, more preferably from 0 to 1 mol %, of hydrogen. The above-described catalysts based on zeolites which have been treated twice with $NH_4$ solution have a long life even without the addition of hydrogen to the feed stream which is customary in the prior art and are therefore particularly well suited for use as DHAM catalysts when the product stream P is recirculated after a very large proportion of the hydrogen formed has been separated off.

EXAMPLE 1

A membrane-electrode assembly which had an active area of 5 cm² and had a membrane based on polybenzimidazole filled with phosphoric acid was used. This membrane is obtainable under the trade name Celtec P® from BASF Fuel Cell GmbH. Gas diffusion electrodes which are obtainable under the trade name ELAT® likewise from BASF Fuel Cell GmbH were used for the anode and the cathode. The anode and the cathode each comprised 1 mg/cm² of platinum. The experiments were carried out at an operating temperature of 160° C. and at atmospheric pressure. The gas mixture was premixed for the separation experiments and comprised 11.40 mol % of hydrogen, 88.10 mol % of methane, 5000 mol ppm of ethene, 100 mol ppm of benzene and 50 mol ppm of ethane. Air was conveyed along the cathode side and the gas mixture was conveyed along the anode side, each at the same flow rate. At different gas flows kept constant in each case, the gas mixture obtained on the permeate side was analyzed by gas chromatography and the current densities were measured.

Table 1 shows the hydrogen conversions and current densities achieved, with the conversion of $H_2$ referring to the amount of $H_2$ separated off in % based on the hydrogen comprised in the anode gas stream.

TABLE 1

| Anode flow [ml/min] | Current density [A/cm²] | Conversion of $H_2$ [%] |
|---|---|---|
| 100 | 0.24 | 33 |
| 200 | 0.26 | 20 |
| 300 | 0.27 | 14 |
| 500 | 0.28 | 6 |
| 1000 | 0.29 | 0.2 |

The invention claimed is:

1. A process for converting at least one aliphatic hydrocarbon having from 1 to 4 carbon atoms into at least one aromatic hydrocarbon, the process comprising:
    (a) reacting a feed stream, E, comprising at least one aliphatic hydrocarbon having from 1 to 4 carbon atoms, in the presence of a catalyst under nonoxidative conditions to give a product stream, P, comprising at least one aromatic hydrocarbon and hydrogen; and
    (b) electrochemically removing at least part of the hydrogen formed in the reacting from the product stream, P, with a gastight membrane-electrode assembly comprising at least one selectively proton-conducting membrane and at least one electrode catalyst on each side of the membrane, wherein at least part of the hydrogen is oxidized to protons over the anode catalyst on a retentate side of the membrane and the protons are, after passing through the membrane on a permeate side, reacted with oxygen to form water over a cathode catalyst, with the oxygen originating from an oxygen-comprising stream, O, which is brought into contact with the permeate side of the membrane.

2. The process of claim 1, wherein the at least one aromatic hydrocarbon formed is separated off from the product stream, P, between the reacting (a) and the electrochemically removing (b).

3. The process of claim 1, wherein the at least one aromatic hydrocarbon formed is separated off from the product stream, P, after the electrochemically removing (b).

4. The process of claim 1, wherein the product stream, P, is recirculated to the process after removal of at least part of the hydrogen formed and the at least one aromatic hydrocarbon.

5. The process of claim 1, wherein the electrochemically removing (b) is carried out at a temperature of from 20 to 1200° C.

6. The process of claim 1, wherein the oxygen-comprising stream, O, comprises at least 15 mol % of oxygen.

7. The process of claim 1, wherein the oxygen-comprising stream, O, comprises air.

8. The process of claim 1, wherein the electrochemically removing (b) is carried out at a pressure of from 0.5 to 10 bar.

9. The process of claim 1, wherein the same pressure prevails on the retentate side and the permeate side in the electrochemically removing (b).

10. The process of claim 1, wherein the selectively proton-conducting membrane comprises at least one membrane selected from the group consisting of a polymer membrane and a ceramic membrane.

11. The process of claim 1, wherein the electrode comprises at least one gas diffusion electrode.

12. The process of claim 1, wherein the feed stream, E, comprises at least 50 mol % of methane.

13. The process of claim 1, wherein the feed stream, E, originates from natural gas.

14. The process of claim 2, wherein the product stream, P, is recirculated to the process after removal of at least part of the hydrogen formed and the at least one aromatic hydrocarbon.

15. The process of claim 2, wherein the electrochemically removing (b) is carried out at a temperature of from 20 to 1200° C.

16. The process of claim 2, wherein the oxygen-comprising stream, O, comprises at least 15 mol % of oxygen.

17. The process of claim 2, wherein the oxygen-comprising stream, O, comprises air.

18. The process of claim 2, wherein the electrochemically removing (b) is carried out at a pressure of from 0.5 to 10 bar.

19. The process of claim 2, wherein the same pressure prevails on the retentate side and the permeate side in the electrochemically removing (b).

20. The process of claim 2, wherein the selectively proton-conducting membrane comprises at least one membrane selected from the group consisting of a polymer membrane and a ceramic membrane.

21. The process of claim 2, wherein the electrode comprises at least one gas diffusion electrode.

22. The process of claim 2, wherein the feed stream, E, comprises at least 50 mol % of methane.

23. The process of claim 2, wherein the feed stream, E, originates from natural gas.

* * * * *